United States Patent [19]

Geria

[11] 4,431,837
[45] Feb. 14, 1984

[54] LONG CHAIN ALIPHATIC HYDROCARBON ETHOXYLATED ALCOHOL BENZOATES

[75] Inventor: Navin Geria, Warren, N.J.

[73] Assignee: Bristol-Myers Company, New York, N.Y.

[21] Appl. No.: 329,091

[22] Filed: Dec. 9, 1981

[51] Int. Cl.$^3$ ............................................. C07C 69/76
[52] U.S. Cl. ................................... 560/112; 424/308; 252/182
[58] Field of Search ..................... 560/112; 424/308; 252/182

[56] References Cited

FOREIGN PATENT DOCUMENTS 1243312  6/1967  Fed. Rep. of Germany ...... 560/112

*Primary Examiner*—Paul J. Killos
*Attorney, Agent, or Firm*—Gabriel P. Katona; Irving Holtzman; George A. Mentis

[57] ABSTRACT

Long chain aliphatic hydrocarbon ethoxylated alcohol benzoates having a small degree of ethoxylation and believed to be of the general formula:

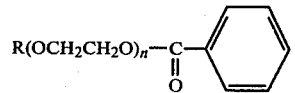

in which:

(a) R is a long chain aliphatic hydrocarbon radical having from about 8 to about 18 carbon atoms and n is a number no greater than about 5.

These are useful as vehicles in pharmaceutical, cosmetic or toiletry preparations.

16 Claims, No Drawings

LONG CHAIN ALIPHATIC HYDROCARBON ETHOXYLATED ALCOHOL BENZOATES

This invention relates to long chain aliphatic hydrocarbon ethoxylated alcohol benzoates having a small degree of ethoxylation. More particularly, it concerns benzoates of the above character having a maximum of 5 moles of ethoxylation with the preferred range being from about 2 moles to about 5 moles of ethoxylation. However, the materials of choice are those that have between about 2 to about 3 moles of ethoxylation.

The aforesaid benzoate esters are believed to be defined by the formula:

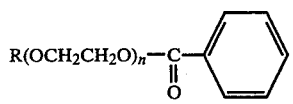 (I)

in which:
(a) R is a long chain aliphatic hydrocarbon radical having from about 8 to about 18 carbon atoms inclusive; and
(b) n is a number no greater than 5.

In the preferred form of this invention, R has from 9 to 15 carbon atoms (optimally from 12 to 15 carbon atoms) inclusive and n has a value of from about 2 to about 5 inclusive. Again, optimally, n has a value of from about 2 to about 3 inclusive.

It is within the scope of this invention to provide a composition involving mixtures of compounds each falling within the definition of Formula I in which the values for R and/or n may be different; that is to say, that the carbon chain length for R or the degree of ethoxylation, n, may vary. In this case, Formula I may also be used to designate such a composition but the values of R and n may be average values for carbon chain length and degree of ethoxylation. Because of this, R and n may sometimes have fractional values.

The compounds of the present invention are useful as vehicles in pharmaceutical, cosmetic or toiletry preparations. To illustrate some types of compositions in which the compounds of Formula I may serve as a vehicle, the following may be mentioned: deodorant sticks, roll-on antiperspirants, stick antiperspirants, cologne, liquid soap, skin cleansing cream, hand lotion, etc. Aside from functioning as a vehicle for compositions of these types, the compounds of this invention also serve as emollients.

It is accordingly an object of the present invention to provide as compositions of matter long chain aliphatic hydrocarbon ethoxylated alcohol benzoates having a small or low degree of ethoxylation.

It is also an object of the present invention to provide compositions of matter in which the aforesaid long chain aliphatic hydrocarbon ethoxylated alcohol benzoates either alone or in combination with other materials, serve as a vehicle for pharmaceutical, cosmetic, toiletry compositions.

Other and more detailed objects of this invention will be apparent from the following description and claims.

The compounds of the present invention may be prepared by esterifying ethoxylated alcohols i.e. adducts of long chain alcohols and ethylene oxide that are believed to be defined by the formula:

$$R(OCH_2CH_2O)_nH \qquad (II)$$

wherein R and n have the same values ascribed to them above in connection with Formula I with a benzoylating agent e.g. benzoyl chloride, benzoic acid or benzoic acid anhydrides. In carrying out these reactions, it is sometimes useful to employ esterification catalyst e.g. methane sulfonic acid, toluene sulfonic acid, etc. To insure the completeness of the reaction, it is desirable to use a molar excess of the benzoylating reactant i.e. benzoyl chloride, benzoic acid or benzoic acid anhydride.

Any ethoxylated alcohol falling within the definition of Formula II may be used in the present invention. A number of such ethoxylated alcohols are available commercially and are sold under the trademark NEODOL from the Shell Chemical Company. The long chain alcohol moiety of these ethoxylated alcohols is generally derived from a mixture of alcohols. The following Table illustrates some of the NEODOL products that are useful in preparing the esters of this invention:

TABLE I

| Alcohol Ethoxylate | Carbon Chain Length R in Formula I | Average Ethylene Oxide group; n in Formula I |
|---|---|---|
| NEODOL 91-2.5 | $C_9, C_{10}, C_{11}$ | 2.5 |
| NEODOL 25-3 | $C_{12}, C_{13}, C_{14}, C_{15}$ | 3 |

By way of further illustration of fatty alcohol ethylene oxide adducts that may be used to prepare the present esters, mention may be made of the product made from a mixture of $C_{12}$ to $C_{15}$ alcohols with 5 moles of ethylene oxide.

These starting materials i.e. the compounds of Formula II are prepared by reacting the corresponding commerical alcohols with the appropriate molar quantity of ethylene oxide. This will vary with the degree of ethoxylation that is desired. A suitable process is described in Satkowski and Hsu in Ind. Eng. Chem. 49, 1875 (1975).

As indicated above, the compounds of this invention of special interest are those that have from about 2 to about 3 moles of ethylene oxide incorporated in the product. The ethoxylated alcohols that wil be employed in this case are those of Formula II in which n has a value of from about 2 to about 3 inclusive.

As also indicated above, the compounds of the present invention are useful as vehicles in pharmaceutical, cosmetic and toiletry preparations. Of special interest is their use of emollient vehicles in deodorant and antiperspirant compositions. For this purpose, the products that are most suitable are those of Formula I in which n has a value of from about 2 to about 3 inclusive.

When used as a vehicle, the quantity of ethoxylated alcohol benzoate of this invention that may be employedmay vary somewhat. Since this may be employed in combination with other vehicles, the level of ethoxylated alcohol benzoate employed will, to some degree, depend upon the other vehicle employed. Similarly, the quantity of other ingredients in the composition will also govern the level of ethoxylated alcohol benzoate utilized. In general, however, this will be in the range of from about 2% to about 50% by weight based on the total weight of the composition.

As previously mentioned, other materials may be used as vehicles in combination with the ethoxylated alcohol benzoates of this invention. By way of example, but not limitation, the following emollient vehicles may be mentioned: liquid hydrocarbon (mineral oil); fatty acid esters (isopropyl myristate, isopropyl palmitate); branched chain fatty acid esters (2-ethyl hexyl palmitate) diesters of dicarboxylic acids (diisopropyl adipate); polyoxy alkylene glycol esters (polypropylene glycol 2000 monooleate); propylene glycol diesters of short chain fatty acids (C8-C10) (Neobee M-20); polyoxyethylene esters (polyoxyethylene(4)lauryl ether (Brij 30), polyoxyethylene fatty acids, polyoxypropylene cetyl ether (procetyl); higher fatty alcohols (oleyl, hexadecyl, lauryl); Silicone Oils (dimethyl polysiloxane, 10–1000 centistokes); Volatile Silicones (e.g. Cyclomethicone 251). Mixtures of the about liquids are equally suitable for the purpose of this invention.

In preparing antiperspirant compositions encompassed in the present invention any of a variety of active antiperspirant materials may be utilized. These include such materials as astringent aluminum or zirconium compound or mixtures thereof; that is, mixtures of aluminum compounds or mixtures of zirconium compounds or mixtures of aluminum compounds with zirconium compounds. Usually, the aluminum or zirconium compounds will take the form of astringent salts. Typical antiperspirant actives include impalpable aluminum chlorhydroxide and aluminum hydroxybromide, aluminum chloride as well as the antiperspirant actives disclosed in U.S. Pat. No. 3,792,068 issued Feb. 12, 1974 to Leudders et al.

The quantity of active antiperspirant material that can be used herein can vary somewhat. All that is required is sufficient quantity of material which will give an effective antiperspirant effect. This will usually fall within the range of from about 10% to about 60% by weight based on the total weight of the composition with the preferred range being from about 15.0% to about 30.0% on the same weight basis.

The compositions of the present invention may also contain other components than those mentioned above. These will depend upon the form that the product takes e.g. a stick as distinguished from a lotion or solution or the use to which the product is to be put. In the case of stick compositions, these may contain waxy materials that form the backbone of the stick. In case of lotions, solutions or the like, such compositions may contain surfactants, solvents, coloring agents, perfumes, preservatives, stabilization agents, bactericides, antioxidants, etc.

Benzoate esters of long chain fatty alcohols have from $C_9$ to $C_{15}$ carbon atoms in the alcohol moiety and their use in antiperspirant compositions has been suggested in the prior art. In this connection, attention is directed to U.S. Pat. Nos. 4,275,222 and 4,278,655. These esters, however, have been found to have heavy potential for staining of skin and therefore, of very little use as a vehicle for antiperspirant compositions.

In the Journal of the American Oil Chemists Society, No. 42, p. 69–71 Gildenberg and Trowbridge discloses the preparation of acetate esters of certain ethylene oxide adducts of fatty alcohols. These are prepared so as to be able to study the distribution of the degree of ethoxylation of the adduct products. No mention is made of the benzoate ester or its usefulness disclosed herein.

The following Examples are given to further illustrate the present invention. It is to be understood, however, that the invention is not limited thereto.

The following terms used in the Examples and elsewhere have the following designation:

NEODOL 25-3: Product obtained from ethoxylation of a mixture of $C_{12}$ to $C_{15}$ fatty alcohols with 3 moles of ethylene oxide.

Irgansan DP 300: Triclosan 5-chloro-2-(2,4-dichlorophenoxy) phenol.

Artemol 202A: $C_{12}$–$C_{15}$ (POE 2) benzoate.

Witconol APM: PPG-3-Myristyl Ether

Castorwax MP 80: Hydrogenated Castor Oil, m.p. 80° C.

Ionol CP: Butylated Hydroxytoluene

Volatile Silicone 7158: Cyclomethacone; cyclic dimethylpolysiloxane.

Rezal: Aluminum/Zirconium Trichlorhydrex Glycine Complex.

Monamid 716: Lauramide DEA; a mixture of ethanolamides of lauric acid conforming generally to the formula $$CH_3(CH_2)_{10}\overset{O}{\underset{\|}{C}}-N(CH_2CH_2OH)_2.$$

Duponol QC: Sodium Lauryl Sulfate.

Ceraphyl 60: Quaternium-22; γ-Gluconamidopropyl Dimethyl-2-Hydroxyethyl Ammonium Chloride.

Arlacel 60: Sorbitan Stearate.

Tween 60: Polysorbate 60 (CAS No. PM 9005-67-8).

Dow Corning 200 Fluid: Dimethacone (CAS No.: PM 9006-65-9).

Foamole B: Minkamidopropyl Dimethylamine; conforms generally to formula $$R\overset{O}{\underset{\|}{C}}-NH-(CH_2)_3-N\overset{CH_3}{\underset{CH_3}{\diagdown}} \quad \text{where } R\overset{O}{\underset{\|}{C}}-$$

represents fatty group derived from mink oil.

Natrosol 250HR: Hydroxyethyl cellulose.

Witconol 308: Aluminum Sesquichlorohydrate.

EXAMPLE 1

330 g (1 mole) of NEODOL 25-3 is dissolved in 1 liter of pyridine. To the well stirred solution 154 g (1.1 mole) of benzoyl chloride is added in rapid dropwise fashion. After addition is complete, the mixture is refluxed with stirring for 2 hours. The cooled solution is slowly poured with vigorous stirring into three liters of ice water. The mixture is stirred for one hour and poured into a separatory funnel. The aqueous lower layer is removed. The upper layer is shaken with 500 ml of 5% sodium carbonate solution, allowed to settle, and the sodium carbonate layer is removed. The sodium carbonate wash is repeated followed by a wash with 500 ml of water. The benzoate layer can then be distilled in vacuum or dried over anhydrous sodium sulfate and used without purification.

EXAMPLE 2

A mixture of 330 g (1 mole) of NEODOL 25-3, 134 g (1.1 mole) of benzoic acid and 3 g of p-toluenesulfonic acid is heated under nitrogen at 170° C. for five hours while allowing the liberated water to be distilled off. At the end of the heating time, the mixture is cooled and washed with sodium carbonate solution and water as described in the previous preparation. The product can be isolated as described in the previous preparation.

EXAMPLE 3

The process of Example 1 is followed except that in place of NEODOL 25-3, the same molar quantities of NEODOL 91-2.5 is used.

EXAMPLE 4

The process of Exmaple 1 is followed except that in place of NEODOL 25-3, the same molar quantities of a mixture of $C_{12}$–$C_{15}$ fatty alcohol adduct with 5 moles of ethylene oxide is employed.

EXAMPLE 5

Clear Deodorant Stick (FN 1775-39A)

| Ingredients | % by Wt. |
| --- | --- |
| Irgasan DP 300 | 0.20 |
| Propylene glycol | 25.00 |
| Artemol 202A | 2.00 |
| Sodium stearate | 8.00 |
| Witconol APM | 59.30 |
| Absolute alcohol | 4.00 |
| D&C Green #5 (0.05% aq. sol.) | 1.50 |
| | 100.00 |

EXAMPLE 6

Dry Application Roll-On Antiperspirant

FN 1775-64

| Ingredients | % by Wt. |
| --- | --- |
| Aluminum zirconium tetrachlorhydrex gly (Wikenol 369) | 24.00 |
| Stearalkonium hectorite (Bentone 27) | 2.10 |
| Colloidal silicon dioxide M-5 | 1.50 |
| 2 Mole Ethoxylate $C_{12}$–$C_{15}$ Alcohol benzoate (Artemol 202A) | 24.85 |
| Alcohol SD-40, anhydrous (Brucine sulfate) | 47.47 |
| Perfume 4330 AD (IFF) | 0.08 |
| | 100.00 |

EXAMPLE 7

Unscented Antiperspirant Stick (FN 1775-81A)

| Ingredients | % by Wt. |
| --- | --- |
| Stearyl alcohol | 9.00 |
| Castorwax MP 80 | 4.00 |
| FT 300 | 2.00 |
| Artemol 202A | 3.00 |
| Ionol CP | 0.05 |
| Volatile Silicone 7158 | 48.95 |
| Talc 5251 | 7.00 |
| Rezal | 26.00 |
| | 100.00 |

EXAMPLE 8

Men's Cologne (FN 1775-87A)

| Ingredients | % by Wt. |
| --- | --- |
| Alcohol (95% SD 40 anhy.) | 60.00 |
| Artemol 202A | 5.00 |
| Perfume 0/705609 | 1.00 |
| Water, deionized | 32.00 |
| Propylene glycol | 1.00 |
| D&C Green #5 (0.1% aq. sol.) | 1.00 |
| | 100.00 |

EXAMPLE 9

Skin Moisturizing Liquid Soap (FN1775-89A)

Skin Moisturizing Liquid Soap (FN 1775-89A)

| Ingredients | % by Wt. |
| --- | --- |
| Monamid 716 | 5.00 |
| Ivory beads | 4.00 |
| Duponol QC | 20.00 |
| Propylene glycol | 1.00 |
| Methyl paraben | 0.20 |
| Petrolatum | 1.00 |
| Ceraphyl 60 | 1.00 |
| Artemol 202A | 5.00 |
| Water, deionized | 62.80 |
| | 100.00 |

EXAMPLE 10

Skin Cleansing Cream (o/w type)

FN 1941-10A

| Ingredients | % by Wt. |
| --- | --- |
| Artemol 202A | 48.8 |
| Beeswax | 15.0 |
| Arlacel 60 | 2.0 |
| Tween 60 | 3.0 |
| Propyl paraben | 0.1 |
| Water, deionized | 30.4 |
| Perfume | 0.5 |
| Methyl paraben | 0.2 |
| | 100.0 |

EXAMPLE 11

Four Drops Hand Lotion

FN 1941-25A

| Ingredients | % by Wt. |
| --- | --- |
| Cetyl alcohol | 1.00 |
| Artemol 202A | 4.00 |
| Dow Corning 200 Fluid | 1.50 |
| Propyl paraben | 0.02 |
| Glyceryl Monostearate (Neutral) | 4.00 |
| Foamole B | 1.00 |
| Natrosol 250 HR | 0.60 |
| Lactic acid 88% | 0.40 |
| Glycerin | 3.00 |
| Methyl paraben | 0.20 |
| Ceraphyl 60 | 1.00 |

| Ingredients | % by Wt. |
|---|---|
| Water, deionized | 83.28 |
| | 100.00 |

EXAMPLE 12

Antiperspirant Composition

FN 1941-55A

| Ingredients | % by Wt. |
|---|---|
| ACH (50%) | 18.0 |
| $AlCl_3.6H_2O$ (50%) | 6.0 |
| Rezal | 35.0 |
| Urea | 0.5 |
| 5 Mole ethoxylated $C_{12}-C_{15}$ alcohol benzoate | 10.0 |
| Alcohol (anhy.) | 30.50 |
| | 100.00 |

EXAMPLE 13

Aluminum Sesquichlorohydrate Antiperspirant Composition (FN 1941-64)

| Ingredients | % by Wt. |
|---|---|
| Wickenol 308 | 22.00 |
| Alcohol (Anhy.) | 50.00 |
| Water, deionized | 8.00 |
| Glycine | 0.50 |
| PPG-3 Myristyl ether | 12.50 |
| Volatile Silicone F 207 | 2.00 |
| Dermol 126 | 5.00 |
| | 100.00 |

Although the invention has been described with reference to specific forms thereof, it will be understood that many changes and modifications may be made without departing from the spirit of this invention.

What is claimed is:

1. Long chain aliphatic hydrocarbon ethoxylated alcohol benzoates containing no more than about 5 moles of ethylene oxide.

2. Long chain aliphatic hydrocarbon ethoxylated alcohol benzoates according to claim 1 in which the aliphatic hydrocarbon moiety contains from about 8 to about 18 carbon atoms inclusive.

3. Long chain aliphatic hydrocarbon ethoxylated alcohol benzoates according to claim 1 in which the aliphatic hydrocarbon moiety contains from about 9 to about 15 carbon atoms inclusive.

4. Long chain aliphatic hydrocarbon ethoxylated alcohol benzoates according to claim 1 in which the aliphatic hydrocarbon moiety contains from about 12 to about 15 carbon atoms inclusive.

5. Long chain aliphatic hydrocarbon ethoxylated alcohol benzoates according to claim 1 in which the degree of ethoxylation corresponds to no more than from about 2 to about 3 moles of ethylene oxide inclusive.

6. Long chain aliphatic hydrocarbon ethoxylated alcohol benzoates according to claim 5 in which the aliphatic hydrocarbon moiety contains from about 9 to about 15 carbon atoms inclusive.

7. Long chain aliphatic hydrocarbon ethoxylated alcohol benzoates according to claim 5 in which the aliphatic hydrocarbon moiety contains from about 12 to about 15 carbon atoms inclusive.

8. Long chain aliphatic hydrocarbon ethoxylated alcohol benzoates of formula:

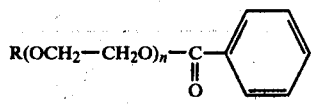

wherein R is a long chain aliphatic hydrocarbon radical havign from about 8 to 18 carbon atoms inclusive and n is a number no greater than about 5.

9. Long chain aliphatic hydrocarbon ethoxylated alcohol benzoates according to claim 8 in which R has from about 9 to about 15 carbon atoms inclusive.

10. Long chain aliphatic hydrocaron ethoxylated alcohol benzoates according to claim 9 in which n has a value of from about 2 to about 5 inclusive.

11. Long chain aliphatic hydrocarbon ethoxylated alcohol benzoates according to claim 9 in which n has a value of from about 2 to about 3 inclusive.

12. Long chain aliphatic hydrocarbon ethoxylated alcohol benzoates according to claim 8 in which R has from about 12 to about 15 carbon atoms inclusive.

13. Long chain aliphatic hydrocarbon ethoxylated alcohol benzoates according to claim 12 in which n has a value of from about 2 to about 5 inclusive.

14. Long chain aliphatic hydrocarbon ethoxylated alcohol benzoates according to claim 12 in which n has a value of from about 2 to about 3 inclusive.

15. As a composition of matter a vehicle having incorporated therein an effective amount of a cosmetic, toiletry, or physiologically active material; said vehcile comprising at least one long chain aliphatic hydrocarobn ethoxylated benzoate as claimed in any one of claims 1 through 14 inclusive.

16. As a composition of matter a vehicle having incorporated therein an effective amount of an antiperspirant active material; said vehicle comprising at least one long chain aliphatic hydrocarbon ethoxylated benzoate as defined in any one of claims 1 through 14 inclusive.

* * * * *

UNITED STATES PATENT AND TRADEMARK OFFICE
CERTIFICATE OF CORRECTION

PATENT NO. : 4,431,837

DATED : February 14, 1984

INVENTOR(S) : Navin Geria

It is certified that error appears in the above-identified patent and that said Letters Patent are hereby corrected as shown below:

Column 2, line 44, "wil" should read -- will --;

Column 2, line 56, "ployedmay" should read -- ployed may --;

Column 4, line 4, "Irgansan DP 300" should read -- Irgasan DP 300 --;

Column 6, line 20, "Skin Moisturizing Liquid Soap (FN 1775-89A) second instance, should be deleted.

Claim 8, line 25, "havign" should read -- having --;

Claim 15, line 48, "vehcile" should read -- vehicle --;

line 50, "drocarobn" should read -- drocarbon --.

Signed and Sealed this

Eighth Day of May 1984

[SEAL]

Attest:

GERALD J. MOSSINGHOFF

Attesting Officer

Commissioner of Patents and Trademarks